(12) United States Patent
Maeshima

(10) Patent No.: US 11,203,203 B2
(45) Date of Patent: Dec. 21, 2021

(54) CONNECTION MECHANISM FOR LIQUID FLOW PATH AND INKJET RECORDING APPARATUS

(71) Applicant: KYOCERA Document Solutions Inc., Osaka (JP)

(72) Inventor: Masanobu Maeshima, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 5 days.

(21) Appl. No.: 17/008,527

(22) Filed: Aug. 31, 2020

(65) Prior Publication Data

US 2021/0060961 A1  Mar. 4, 2021

(30) Foreign Application Priority Data

Sep. 3, 2019  (JP) .............................. JP2019-160516

(51) Int. Cl.
| | | |
|---|---|---|
| B41J 2/175 | (2006.01) | |
| A61M 39/24 | (2006.01) | |
| F16L 37/40 | (2006.01) | |

(52) U.S. Cl.
CPC .......... *B41J 2/17523* (2013.01); *A61M 39/24* (2013.01); *B41J 2/17503* (2013.01); *B41J 2/17509* (2013.01); *B41J 2/17513* (2013.01); *B41J 2/17596* (2013.01); *F16L 37/40* (2013.01)

(58) Field of Classification Search
CPC .... B41J 2/175; B41J 2/17503; B41J 2/17513; B41J 2/17523; B41J 2/17596; A61M 39/24; F16L 37/40
See application file for complete search history.

(56) References Cited

U.S. PATENT DOCUMENTS

| | | | | |
|---|---|---|---|---|
| 6,170,939 B1* | 1/2001 | Ujita | .................... | B41J 2/17513 347/86 |
| 6,390,611 B1* | 5/2002 | Kobayashi | ............... | B41J 2/175 347/84 |
| 6,612,689 B2* | 9/2003 | Suenaga | .............. | B41J 2/17509 347/85 |

(Continued)

FOREIGN PATENT DOCUMENTS

JP    2016-83832 A    5/2016

OTHER PUBLICATIONS

Extended European Search Report dated Jan. 11, 2021, issued by the European Patent Office in corresponding application EP 20193978.2.

*Primary Examiner* — Anh T Vo
(74) *Attorney, Agent, or Firm* — Stein IP, LLC

(57) ABSTRACT

In a connection mechanism for a liquid flow path, in a case of connecting a container to an apparatus main body, a slide portion causes a first open/close valve to move to establish communication of the liquid flow path, and a first main body portion causes the slide portion to move to disconnect an air flow path from the liquid flow path. In the connection mechanism for the liquid flow path, in a case of disconnecting the container from the apparatus main body, a second biasing member biases the slide portion to connect the air flow path to the liquid flow path, and the first main body portion is separated from the slide portion, so that a first biasing member biases the first open/close valve to close a part of the liquid flow path included in the first main body portion.

10 Claims, 9 Drawing Sheets

(56) References Cited

U.S. PATENT DOCUMENTS

2010/0002061 A1* 1/2010 Shibano .............. B41J 2/17509
 347/86
2015/0224785 A1 8/2015 Kobayashi

* cited by examiner

CONNECTION MECHANISM FOR LIQUID FLOW PATH AND INKJET RECORDING APPARATUS

INCORPORATION BY REFERENCE

This application is based upon and claims the benefit of priority from the corresponding Japanese Patent Application No. 2019-160516 filed on Sep. 3, 2019, the contents of which are incorporated herein by reference.

BACKGROUND

The present disclosure relates to a connection mechanism for a liquid flow path and an inkjet recording apparatus including the connection mechanism for a liquid flow path.

An inkjet recording apparatus may use a container that contains an ink liquid to be supplied to a main body of the apparatus and is mountable/demountable with respect to the apparatus main body. A connection mechanism for a liquid flow path is disposed in a connection section of the liquid flow path between the apparatus main body and the container.

In the above-described connection mechanism for a liquid flow path, in a case where the container is disconnected and removed from the apparatus main body, the liquid flow path is closed by an open/close valve, and thus the ink liquid is prevented from flowing out to the outside. There has been a fear, however, that in a case where the container is disconnected from the apparatus main body, a slight amount of ink liquid remaining in a connection section between a distal end of a container-side connection portion and a distal end of an apparatus main body-side connection portion might leak to the outside. To address this issue, there have been proposed techniques for suppressing leakage of a liquid remaining in the connection section in the connection mechanism for a liquid flow path.

For example, a joint mechanism for an ink flow path in a conventional inkjet recording apparatus includes a first joint portion provided on an ink container side and a second joint portion provided on an apparatus main body side. The first joint portion includes a container-side valve that opens/closes the ink flow path. The second joint portion includes a tube-shaped slide portion that is used for connection of the ink flow path. Further, in a case of removing the ink container from the apparatus main body, the first joint portion moves in such a direction as to be separated from the second joint portion, and thus after the container-side valve closes the ink flow path, the slide portion moves in such a direction as to increase an internal volume of the second joint portion. By this configuration, ink remaining at a distal end of the first joint portion and at a distal end of the second joint portion is sucked into the second joint portion, and thus leakage of the ink to the outside is suppressed.

SUMMARY

A connection mechanism for a liquid flow path according to one aspect of the present disclosure is disposed in a connection section of a liquid flow path between an apparatus main body and a container that contains a liquid to be supplied to the apparatus main body through suction of the liquid as an action from the apparatus main body and is mountable/demountable with respect to the apparatus main body. The connection mechanism for the liquid flow path includes a first connection portion and a second connection portion. The first connection portion is provided in the container. The second connection portion is provided in the apparatus main body, the first connection portion being mountable/demountable to/from the second connection portion. The first connection portion includes a first main body portion, a first open/close valve, and a first biasing member. The first main body portion includes therein a part of the liquid flow path. The first open/close valve is disposed in the first main body portion and opens/closes the liquid flow path. The first biasing member biases the first open/close valve in such a direction as to close the liquid flow path. The second connection portion includes a second main body portion, a slide portion, an air flow path, and a second biasing member. The slide portion is disposed in the second main body portion so as to be movable relative to the second main body portion and includes therein another part of the liquid flow path. The air flow path is disposed between the second main body portion and the slide portion and is switched by movement of the slide portion between a state of being connected to the liquid flow path and a state of being disconnected from the liquid flow path. The second biasing member biases the slide portion in such a direction as to connect the air flow path to the liquid flow path. In said connection mechanism for the liquid flow path, in a case of connecting the container to the apparatus main body, the first main body portion is inserted in the second main body portion so that a distal end of the first main body portion is brought into contact with a distal end of the slide portion, the slide portion causes the first open/close valve to move against a biasing force of the first biasing member to open the first open/close valve, thus establishing communication between the part of the liquid flow path included in the first main body portion and the other part of the liquid flow path included in the slide portion, and the first main body portion causes the slide portion to move against a biasing force of the second biasing member to disconnect the air flow path from the liquid flow path. Further, in a case of disconnecting the container from the apparatus main body, a contact pressure between the first main body portion and the slide portion is decreased, so that the second biasing member biases the slide portion to move, thus connecting the air flow path to the liquid flow path, the first main body portion is separated from the slide portion, so that the first biasing member biases the first open/close valve to close the part of the liquid flow path included in the first main body portion, and then the first main body portion is taken out from inside the second main body portion.

BRIEF DESCRIPTION OF THE DRAWINGS

FIG. 5 is a perspective view of an ink container of the ink supply portion shown in

FIG. 3.

DETAILED DESCRIPTION

With reference to the appended drawings, the following describes embodiments of the present disclosure. The present disclosure, however, is not limited to the description below.

Figure 1:
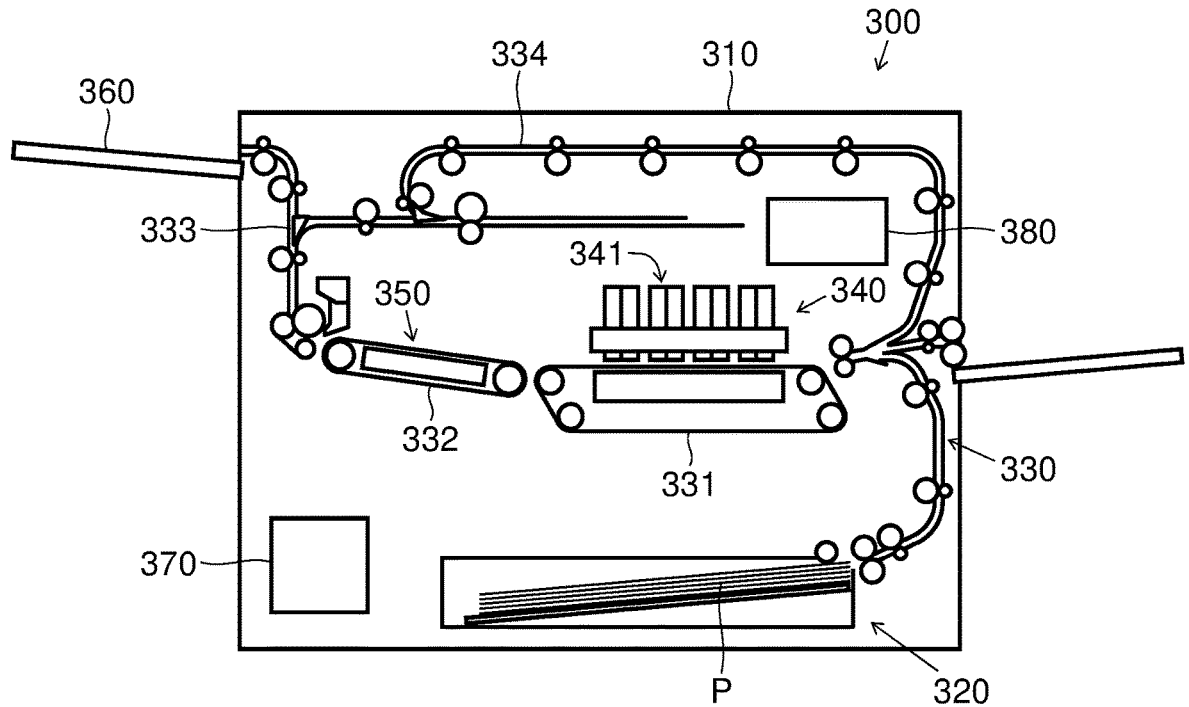
FIG. 1 is a sectional view showing a schematic configuration of an inkjet recording apparatus according to an embodiment of the present disclosure.
Figure 2:
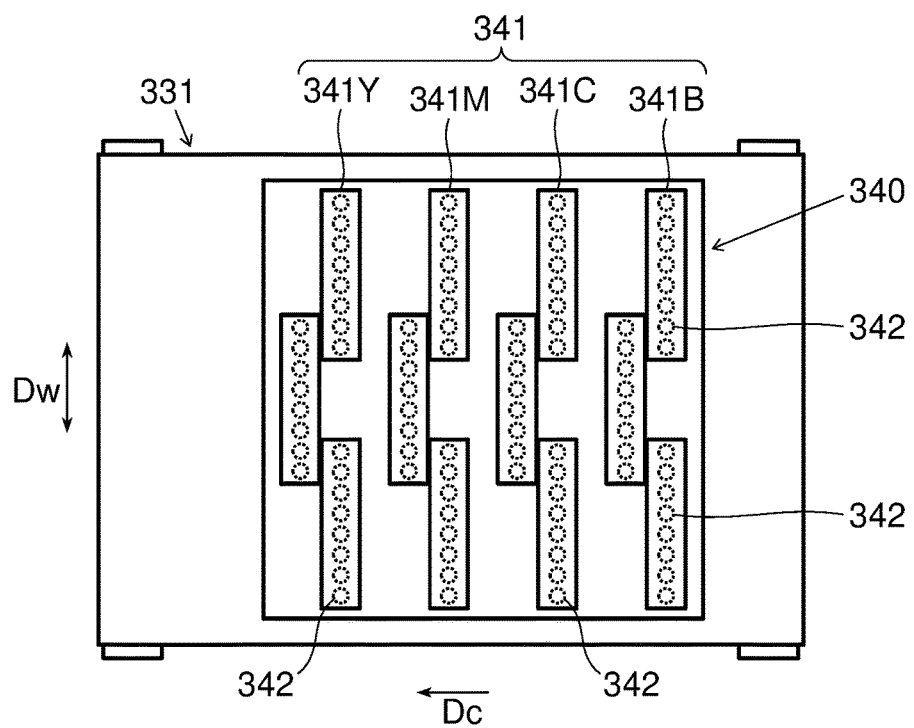
FIG. 2 is a plan view of a recording portion of the inkjet recording apparatus shown in FIG. 1.

FIG. 1 is a sectional view showing a schematic configuration of an inkjet recording apparatus 300 according to an embodiment. FIG. 2 is a plan view of a recording portion 340 of the inkjet recording apparatus 300 shown in FIG. 1. The inkjet recording apparatus 300 is, for example, an inkjet recording-type printer. As shown in FIG. 1 and FIG. 2, the inkjet recording apparatus 300 includes an apparatus main body 310, a sheet feed portion 320, a sheet conveyance portion 330, a recording portion 340, a drying portion 350, a sheet discharge portion 360, and a control portion 370.

The sheet feed portion 320 contains a plurality of sheets (recording media) P and feeds them out one by one separately during recording. The sheet conveyance portion 330 conveys a sheet P, among the plurality of sheets P, fed out from the sheet feed portion 320 to the recording portion 340 and the drying portion 350 and further discharges the sheet P that has been subjected to recording and drying to the sheet discharge portion 360. The sheet conveyance portion 330 includes a first belt conveyance portion 331 and a second belt conveyance portion 332. The first belt conveyance portion 331 and the second belt conveyance portion 332 each convey the sheet P being held by absorption on an upper surface of an endless belt. In a case of performing double-sided recording, by use of a branch portion 333, the sheet conveyance portion 330 sorts the sheet P whose first side has been subjected to recording and drying into an inverse conveyance portion 334 in which a conveyance direction of the sheet P is switched and front and back sides of the sheet P are inverted, and the sheet P in that state is further conveyed again to the recording portion 340 and the drying portion 350.

The recording portion 340 is opposed to the sheet P being conveyed while being held by absorption on an upper surface of the first belt conveyance portion 331 and is disposed above the first belt conveyance portion 331 at a prescribed distance therefrom. The recording portion 340 includes a line-type inkjet recording head 341. The recording head 341 includes recording heads 341B, 341C, 341M, and 341Y corresponding to four colors of black, cyan, magenta, and yellow, respectively. For each of the recording heads 341B, 341C, 341M, and 341Y of the respective colors, a plurality of (for example, three) recording heads 341 are arrayed in a staggered manner along a sheet width direction Dw orthogonal to a sheet conveyance direction Dc.

Each of the recording heads 341B, 341C, 341M, and 341Y includes, in an ink ejection portion provided at a bottom thereof, a plurality of ink ejection nozzles 342. The plurality of ink ejection nozzles 342 are arranged in a row along the sheet width direction Dw and are capable of ejecting ink over an entire recording region. The recording portion 340 sequentially ejects ink from the recording heads 341B, 341C, 341M, and 341Y of the four colors toward the sheet P being conveyed by the first belt conveyance portion 331 so as to record a full-color image or a monochrome image on the sheet P.

The drying portion 350 is disposed on a downstream side of the recording portion 340 in a sheet conveyance direction and is provided with the second belt conveyance portion 332. In the drying portion 350, the sheet P on which an ink image has been recorded in the recording portion 340 is conveyed while being held by absorption on the second belt conveyance portion 332, and ink on the sheet P is dried during this conveyance.

The control portion 370 includes a CPU and a storage portion, which are not shown, and other unshown electronic circuits and electronic components. Based on a control program or control data stored in the storage portion, the CPU controls operations of various constituent elements provided in the inkjet recording apparatus 300 so as to perform processes related to functions of the inkjet recording apparatus 300. The sheet feed portion 320, the sheet conveyance portion 330, the recording portion 340, and the drying portion 350 individually receive commands from the control portion 370 and perform recording on the sheet P in synchronization with each other. The storage portion is constituted by, for example, a combination of a non-volatile storage device such as a program ROM (read-only memory) or data ROM and a volatile storage device such as a RAM (random-access memory), which are not shown.

Figure 3:
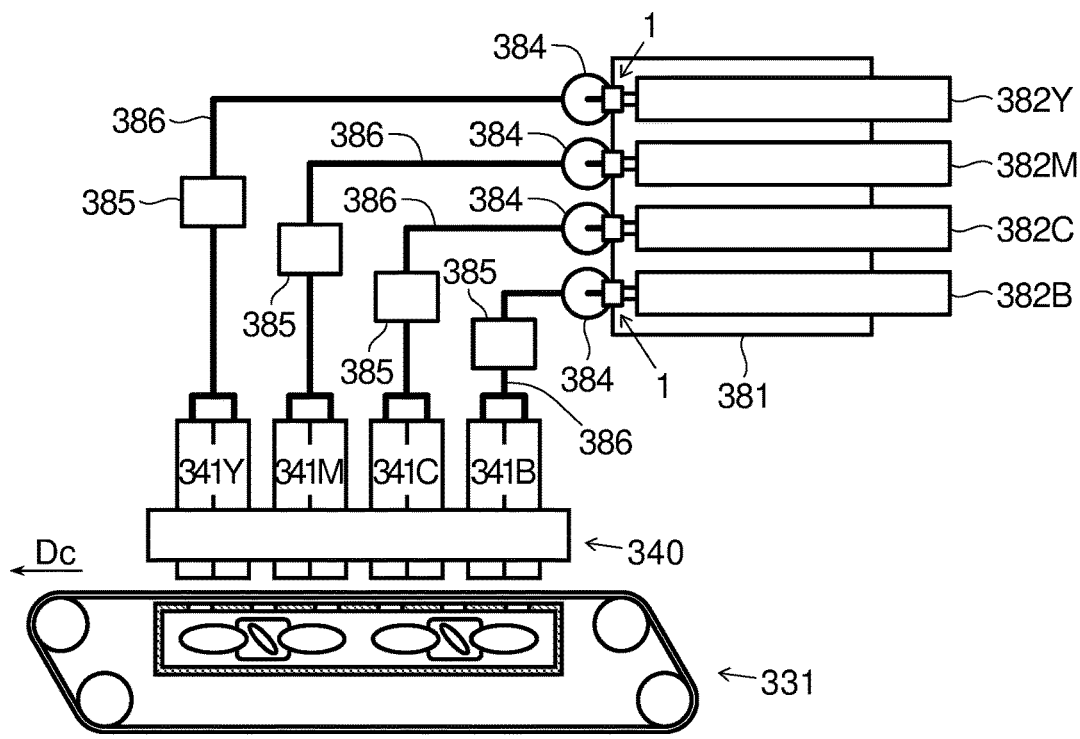
FIG. 3 is a schematic structural view showing surroundings of the recording portion of the inkjet recording apparatus shown in FIG. 1.
Figure 4:
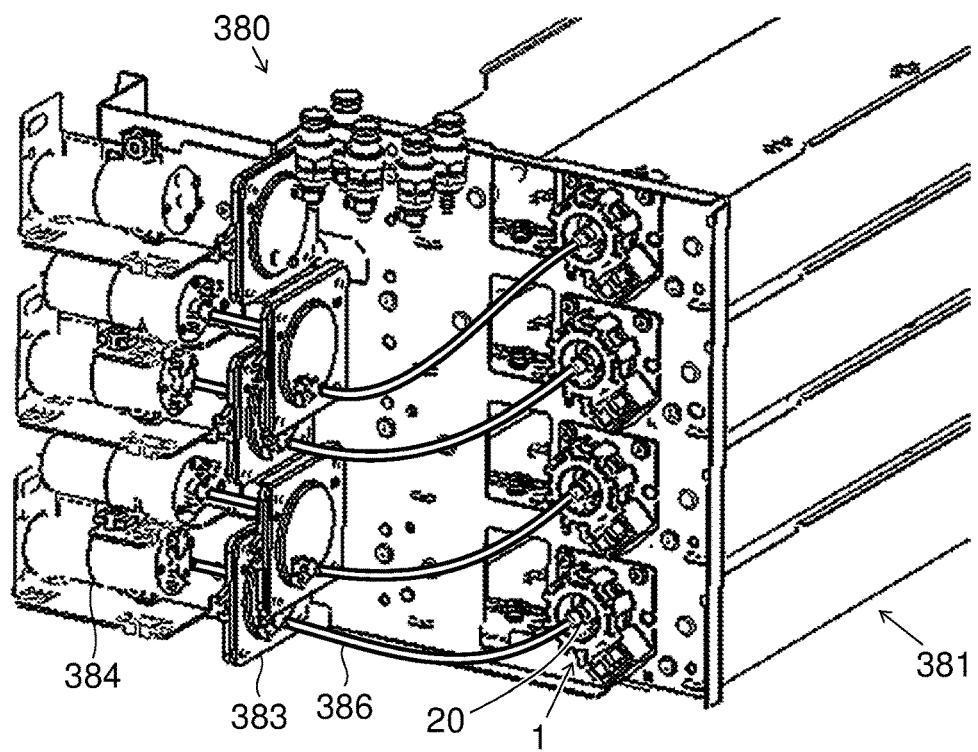
FIG. 4 is a perspective view of an ink supply portion shown in FIG. 3.
Figure 5:
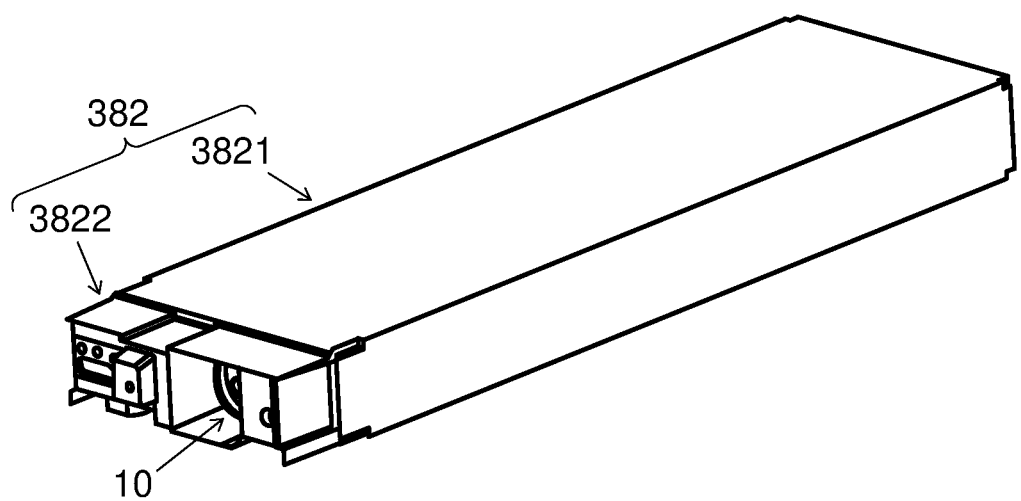

Next, with reference FIG. 3, FIG. 4, and FIG. 5, a description is given of a configuration of an ink supply portion 380 of the inkjet recording apparatus 300. FIG. 3 is a schematic structural view showing surroundings of the recording portion 340 of the inkjet recording apparatus 300 shown in FIG. 1. FIG. 4 is a perspective view of the ink supply portion 380 shown in FIG. 3. FIG. 5 is a perspective view of an ink container 382 of the ink supply portion 380 shown in FIG. 3.

The ink supply portion 380 is disposed, for example, above the recording portion 340. As shown in FIG. 3, FIG. 4, and FIG. 5, the ink supply portion 380 includes a container rack 381, the ink container 382, a connection mechanism 1, a filter 383, a suction pump 384, and a sub-ink tank 385. Each of these constituent elements is individually provided so as to correspond to each of the four colors of black (B), cyan (C), magenta (M), and yellow (Y). Identification symbols "B," "C," "M," and "Y" representing the respective colors may be omitted unless there is a particular need for limitation.

The container rack 381 houses the ink container (a container) 382. The ink container 382 is mountable/demountable with respect to the container rack 381. That is, the ink container 382 is mountable/demountable with respect to the apparatus main body 310.

The ink container 382 contains ink (a liquid) to be supplied to the apparatus main body 310 through suction of the ink by the suction pump 384 on an apparatus main body 310 side. The ink container 382 includes an ink pack housing portion 3821 and an ink outflow portion 3822, which are shown in FIG. 5. The ink container 382 is a substantially rectangular parallelepiped-shaped box body formed by combining the ink pack housing portion 3821 with the ink outflow portion 3822 and houses therein an unshown ink pack.

The ink pack housing portion 3821 has a rectangular tube shape whose one end in a longitudinal direction thereof is open and whose other end in that direction is closed. The ink pack housing portion 3821 is made of, for example, cardboard and houses an ink pack in which an ink liquid is sealed.

The ink outflow portion 3822 is disposed at the open one end of the ink pack housing portion 3821 in the longitudinal direction thereof so as to block an opening at the one end. The ink outflow portion 3822 is made of, for example, a synthetic resin such as polyethylene and is fastened to the ink pack housing portion 3821 with an adhesive tape or the like. The ink outflow portion 3822 is configured to allow ink in the ink pack to flow out to the outside.

The connection mechanism 1 is a connection mechanism for an ink flow path disposed in a connection section of an ink flow path (a liquid flow path) between the container rack 381 provided in the apparatus main body 310 and the ink container 382. A configuration of the connection mechanism 1 will be described later in detail.

By use of an ink supply tube 386, the ink container 382 is connected to the recording head 341 via the connection mechanism 1, the filter 383, the suction pump 384, and the sub-ink tank 385.

The suction pump 384 is formed of, for example, a diaphragm pump, sucks ink from the ink container 382 to convey the ink to the sub-ink tank 385, and functions as a backflow prevention valve that prevents the ink from flowing in an opposite direction. The sub-ink tank 385 temporarily retains the ink and then supplies the ink to the recording head 341.

Figure 6:
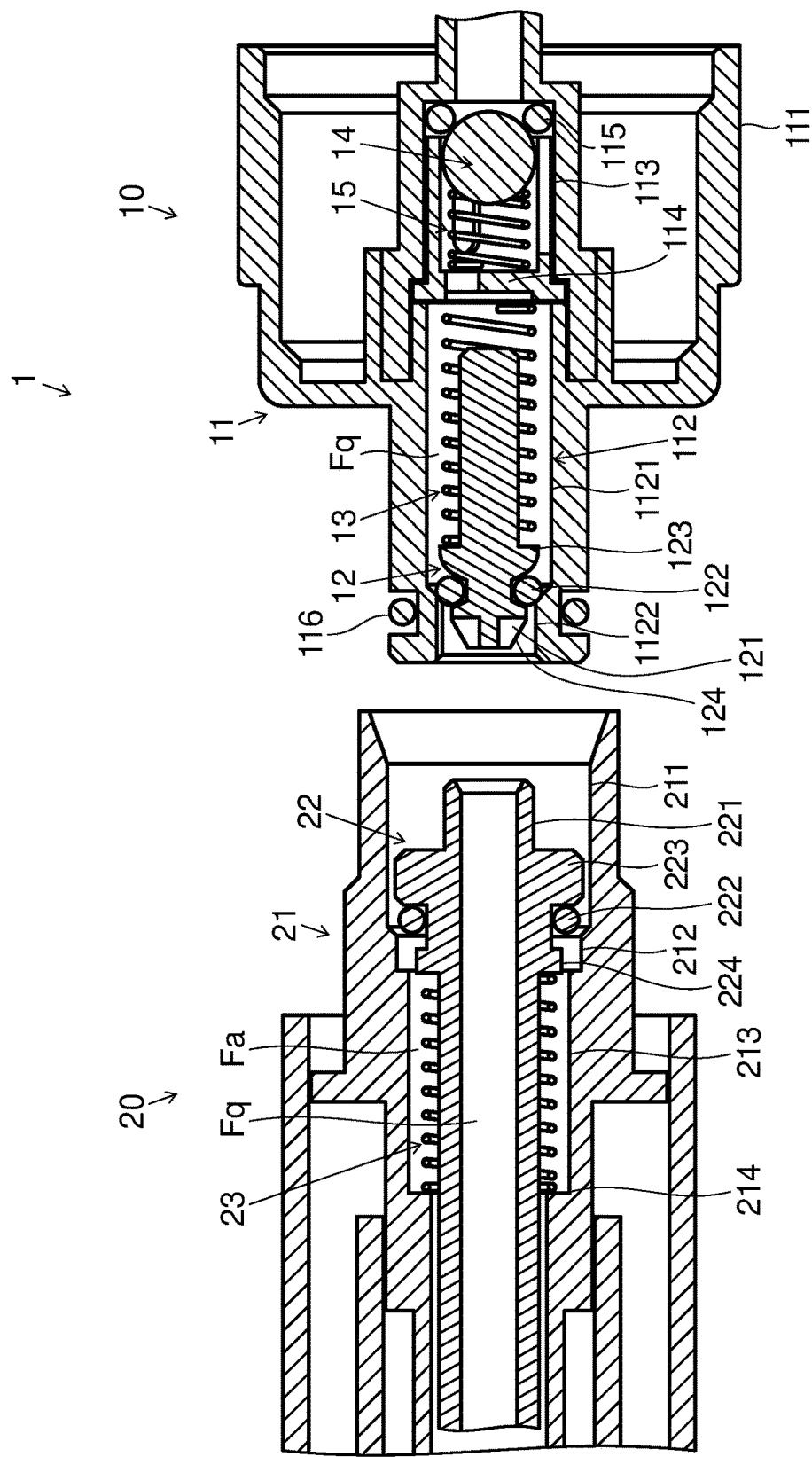
FIG. 6 is a sectional view showing a connection mechanism for an ink flow path according to a first embodiment of the present disclosure.
Figure 7:
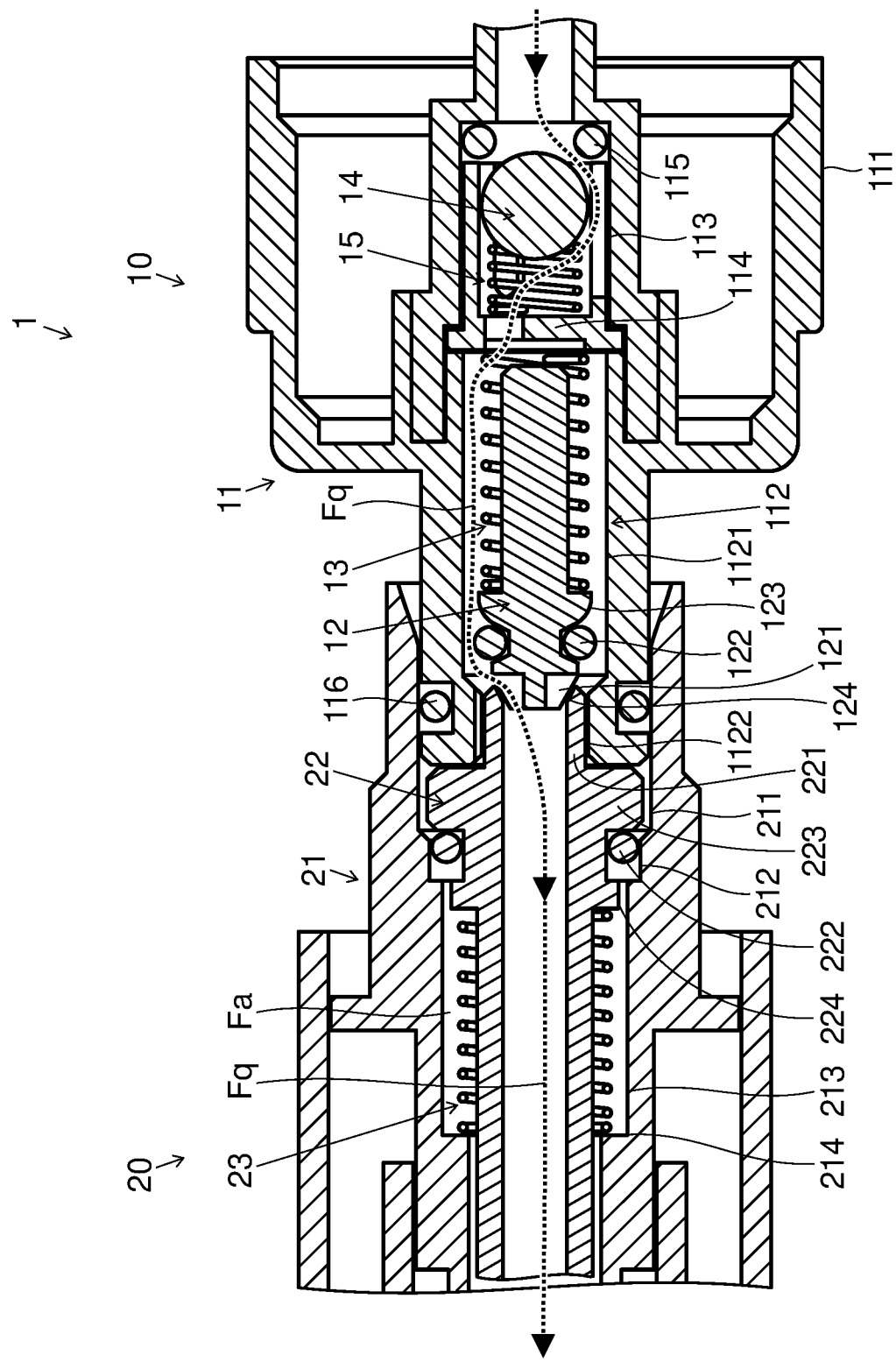
FIG. 7 is a sectional view showing the connection mechanism for an ink flow path according to the first embodiment of the present disclosure, which illustrates a state where communication of the ink flow path is established.
Figure 8:
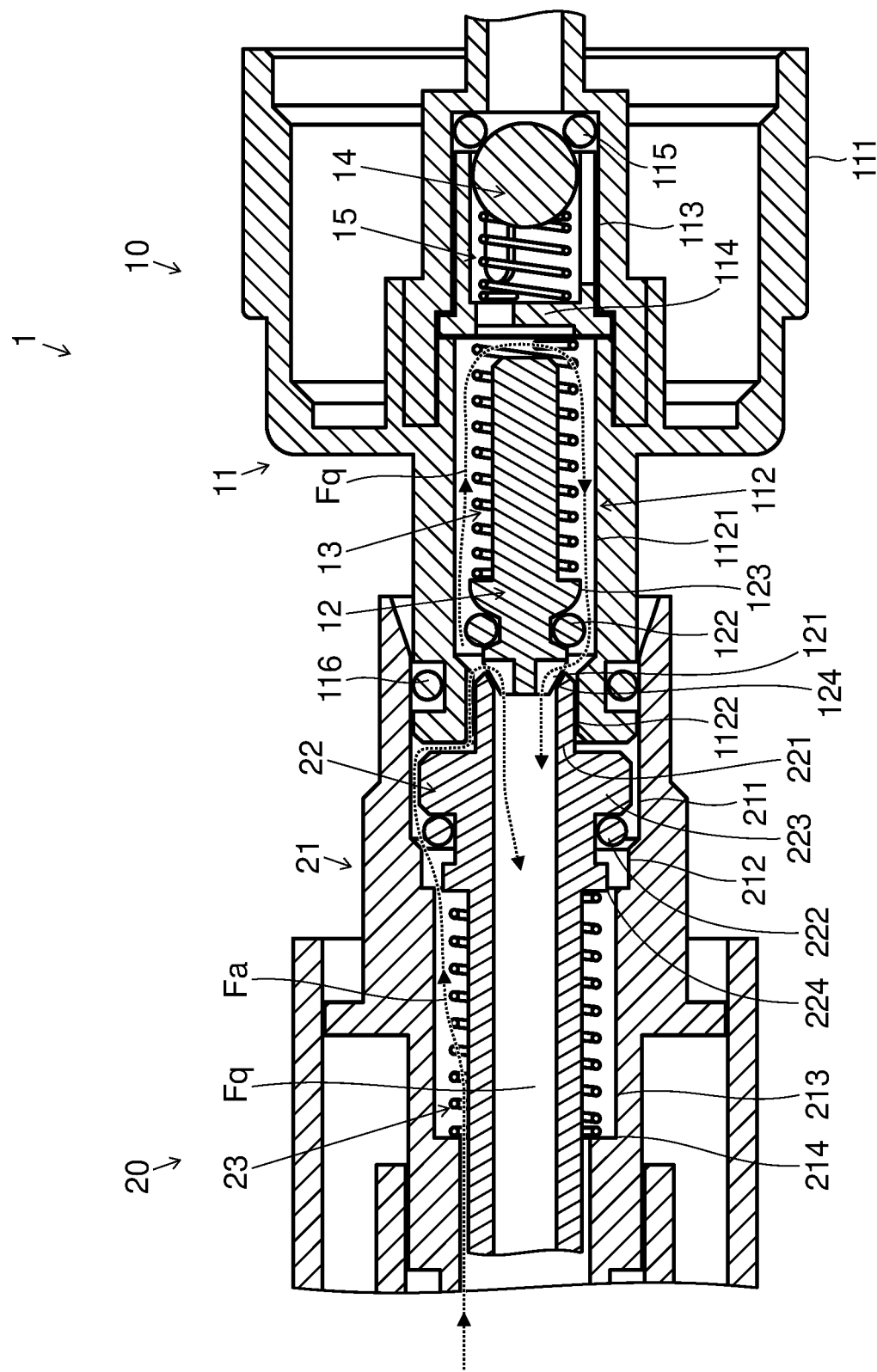
FIG. 8 is a sectional view showing the connection mechanism for an ink flow path according to the first embodiment of the present disclosure, which illustrates a state where an air flow path is connected to the ink flow path.

Next, with reference to FIG. 6, FIG. 7, and FIG. 8, a description is given of the configuration of the connection mechanism 1 for an ink flow path according to a first embodiment. FIG. 6 is a sectional view showing the connection mechanism 1 for an ink flow path Fq according to the first embodiment. FIG. 7 is a sectional view showing the connection mechanism 1 for the ink flow path Fq according to the first embodiment, which illustrates a state where communication of the ink flow path Fq is established. FIG. 8 is a sectional view showing the connection mechanism 1 for the ink flow path Fq according to the first embodiment, which illustrates a state where an air flow path Fa is connected to the ink flow path Fq. An ink supply direction is directed from a first connection portion 10 toward a second connection portion 20 shown in FIG. 6, FIG. 7, and FIG. 8.

As described earlier, the connection mechanism 1 for an ink flow path (a liquid flow path) is disposed in the connection section of an ink flow path between the container rack 381 provided in the apparatus main body 310 and the ink container 382. As shown in FIG. 6, FIG. 7, and FIG. 8, the connection mechanism 1 for the ink flow path Fq includes the first connection portion 10 and the second connection portion 20.

The first connection portion 10 is provided in the ink container 382 and protrudes toward the outside of the ink container 382 (see FIG. 5). The first connection portion 10 is an ink outflow port of the ink container 382, which is disposed in the ink outflow portion 3822 of the ink container 382. The first connection portion 10 includes a first main body portion 11, a first open/close valve 12, a first biasing member 13, a first backflow prevention valve 14, and a third biasing member 15.

The first main body portion 11 includes therein a part of the ink flow path Fq. The first main body portion 11 includes a container coupling portion 111, an open/close valve housing portion 112, a backflow prevention valve housing portion 113, a partition wall 114, a seal member 115, and a seal member 116.

The container coupling portion 111 is formed in a cylindrical shape whose center axis extends in a direction directed from the ink container 382 toward the container rack 381. The container coupling portion 111 includes an unshown screw provided on, for example, an inner circumferential surface thereof and is coupled to the ink outflow portion 3822 by use of said screw.

The open/close valve housing portion 112 and the backflow prevention valve housing portion 113 are disposed at a radial center of the container coupling portion 111. The open/close valve housing portion 112 and the backflow prevention valve housing portion 113 are both formed in a cylindrical shape and are disposed in the order of the backflow prevention valve housing portion 113 and the open/close valve housing portion 112 from an upstream side in the ink supply direction along the center axis of the container coupling portion 111. The first open/close valve 12 and the first biasing member 13 are housed in the open/close valve housing portion 112. The first backflow prevention valve 14 and the third biasing member 15 are housed in the backflow prevention valve housing portion 113.

The open/close valve housing portion 112 includes therein a large inner diameter portion 1121 and a small inner diameter portion 1122. The large inner diameter portion 1121 has an inner diameter larger than that of the small inner diameter portion 1122. The small inner diameter portion 1122 is disposed on a downstream side of the large inner diameter portion 1121 in the ink supply direction so as to be continuous with the large inner diameter portion 1121. A downstream end of the small inner diameter portion 1122 in the ink supply direction is a downstream end of each of the first main body portion 11 and the open/close valve housing portion 112 in the ink supply direction and is open to the outside. The large inner diameter portion 1121 has an inner diameter larger than an outer diameter of an after-mentioned seal member 122 of the first open/close valve 12. The small inner diameter portion 1122 has an inner diameter smaller than the outer diameter of the seal member 122 of the first open/close valve 12.

The partition wall 114 is provided between the open/close valve housing portion 112 and the backflow prevention valve housing portion 113. The partition wall 114 divides the open/close valve housing portion 112 from the backflow prevention valve housing portion 113 in the ink supply direction. The partition wall 114 has a plurality of holes for ink to flow therethrough, which penetrate through the partition wall 114 in the ink supply direction.

The seal member 115 is disposed at an inner circumferential part of the backflow prevention valve housing portion 113 on an upstream side of the first backflow prevention valve 14 in the ink supply direction. The seal member 115 is an O-ring formed of, for example, an elastic member of rubber or the like, and an outer circumferential part thereof is in tight contact with an inner circumferential surface of the backflow prevention valve housing portion 113.

The seal member 116 is disposed at an outer circumferential part of the downstream end of the first main body portion 11 in the ink supply direction. The seal member 116 is an O-ring formed of, for example, an elastic member of rubber or the like, and an inner circumferential part thereof is in tight contact with an outer circumferential surface of the first main body portion 11. When the first main body portion 11 is inserted in a second main body portion 21, an outer circumferential part of the seal member 116 comes in contact with an inner circumferential part of an after-mentioned large inner diameter portion 211 of the second main body portion 21.

The first open/close valve 12 is housed in the open/close valve housing portion 112. That is, the first open/close valve 12 is disposed in the first main body portion 11. The first open/close valve 12 is formed in substantially a rod shape extending along a center axis of the cylindrical open/close valve housing portion 112. In the open/close valve housing portion 112, the first open/close valve 12 is movable in the ink supply direction. The first open/close valve 12 includes an ink passage groove 121, the seal member 122, and a flange portion 123.

The ink passage groove 121 is disposed at an outer circumferential part of a downstream end of the first open/close valve 12 in the ink supply direction. The ink passage groove 121 extends along the ink supply direction, and a plurality of ink passage grooves 121 are arranged in a circumferential direction of the first open/close valve 12 so as to be spaced from each other. The outer circumferential part of the downstream end of the first open/close valve 12 in the ink supply direction includes an inclined portion 124 whose diameter decreases from the upstream side toward a downstream side in the ink supply direction. The ink passage grooves 121 extend from an upstream end to a downstream end of said inclined portion 124 in the ink supply direction.

The seal member 122 is disposed at an outer circumferential part of the first open/close valve 12 on an upstream side of the ink passage grooves 121 in the ink supply direction. The seal member 122 is an O-ring formed of, for example, an elastic member of rubber or the like, and an inner circumferential part thereof is in tight contact with an outer circumferential surface of the first open/close valve 12. The seal member 122 has an outer diameter smaller than an inner diameter of the large inner diameter portion 1121 of the open/close valve housing portion 112 and larger than an inner diameter of the small inner diameter portion 1122 thereof.

The seal member 122 of the first open/close valve 12 is located in the large inner diameter portion 1121 of the open/close valve housing portion 112 in the ink supply direction. When the first open/close valve 12 moves to the downstream side in the ink supply direction, an outer circumferential part of the seal member 122 comes in contact with an inner circumferential part of the small inner diameter portion 1122 of the open/close valve housing portion 112. Thus, the ink flow path Fq is closed at a location of the seal member 122. That is, the first open/close valve 12 opens/closes the ink flow path Fq.

In the first open/close valve 12, the flange portion 123 is provided on an upstream side of a disposition location of the seal member 122 in the ink supply direction. One end of the first biasing member 13 is in contact with a side surface of the flange portion 123 facing the upstream side in the ink supply direction.

The first biasing member 13 is disposed on an upstream side of the flange portion 123 of the first open/close valve 12 in the ink supply direction. The first biasing member 13 is formed of, for example, a compression coil spring, a coil axis of which extends along the center axis of the open/close valve housing portion 112, and an upstream part of the first open/close valve 12 in the ink supply direction is inserted in a coil center thereof.

An upstream end of the first biasing member 13 in the ink supply direction is in contact with a side surface of the partition wall 114 facing the downstream side in the ink supply direction. A downstream end of the first biasing member 13 in the ink supply direction is in contact with the side surface of the flange portion 123 of the first open/close valve 12 facing the upstream side in the ink supply direction. As described earlier, the seal member 122 comes in contact with the inner circumferential part of the small inner diameter portion 1122 of the open/close valve housing portion 112, and thus the ink flow path Fq is closed at the location of the seal member 122. The first biasing member 13 biases the first open/close valve 12 in such a direction as to close the ink flow path Fq.

The first backflow prevention valve 14 is formed in a spherical shape and is housed in the backflow prevention valve housing portion 113. In the backflow prevention valve housing portion 113, the first backflow prevention valve 14 is movable in the ink supply direction. When moving to the upstream side in the ink supply direction, the first backflow prevention valve 14 comes in contact to an inner circumferential part of the seal member 115. Thus, the first backflow prevention valve 14 prevents a backflow of ink in the ink flow path Fq.

The third biasing member 15 is disposed on a downstream side of the first backflow prevention valve 14 in the ink supply direction. The third biasing member 15 is formed of, for example, a compression coil spring, a coil axis of which extends along a center axis of the backflow prevention valve housing portion 113.

An upstream end of the third biasing member 15 in the ink supply direction is in contact with the spherical first backflow prevention valve 14. A downstream end of the third biasing member 15 in the ink supply direction is in contact with a side surface of the partition wall 114 facing the upstream side in the ink supply direction. As described earlier, the first backflow prevention valve 14 comes in contact with the inner circumferential part of the seal member 115, thus preventing a backflow at a location of the seal member 115. The third biasing member 15 biases the first backflow prevention valve 14 in such a direction as to prevent a backflow of ink in the ink flow path Fq.

The second connection portion 20 is provided in the container rack 381 (see FIG. 4). The first connection portion 10 is mountable/demountable to/from the second connection portion 20. The second connection portion 20 is an ink inflow port of the container rack 381. The second connection portion 20 includes a second main body portion 21, a slide portion 22, and a second biasing member 23. The second connection portion 20 further includes an air flow path Fa.

The second main body portion 21 includes therein a part of the ink flow path Fq. The second main body portion 21 is formed in a cylindrical shape whose center axis extends in a direction directed from the container rack 381 toward the ink container 382. The second main body portion 21 is coupled at a downstream part thereof in the ink supply direction to the container rack 381. The slide portion 22 and the second biasing member 23 are housed in the second main body portion 21.

The second main body portion 21 includes therein a large inner diameter portion 211, a small inner diameter portion 212, a biasing member housing portion 213, and a stepped portion 214.

The large inner diameter portion 211 has an inner diameter larger than that of the small inner diameter portion 212. The large inner diameter portion 211 is disposed on an upstream side of the small inner diameter portion 212 in the ink supply direction so as to be continuous with the small inner diameter portion 212. An upstream end of the large inner diameter portion 211 in the ink supply direction is an upstream end of the second main body portion 21 in the ink supply direction and is open to the outside. The large inner diameter portion 211 has an inner diameter larger than an outer diameter of an after-mentioned seal member 222 of the slide portion 22. The small inner diameter portion 212 has an inner diameter smaller than an outer diameter of the seal member 222 of the slide portion 22.

The biasing member housing portion 213 is disposed on a downstream side of the small inner diameter portion 212 in the ink supply direction so as to be continuous with the small inner diameter portion 212 The biasing member housing portion 213 is formed in a cylindrical shape and houses the second biasing member 23 therein.

The stepped portion 214 is disposed on a downstream side of the biasing member housing portion 213 in the ink supply direction so as to be continuous with the biasing member housing portion 213. The stepped portion 214 is so stepped that an inner diameter of a part downstream of the biasing member housing portion 213 in the ink supply direction is even smaller than an inner diameter of the biasing member housing portion 213.

The slide portion 22 is disposed in the second main body portion 21. The slide portion 22 is formed in a cylindrical shape extending along the center axis of the second main body portion 21 and includes therein a part of the ink flow path Fq. The slide portion 22 is movable in the ink supply direction relative to the second main body portion 21. The slide portion 22 includes an open/close valve contact portion 221, the seal member 222, a first flange portion 223, and a second flange portion 224.

The open/close valve contact portion 221 is provided at an upstream end of the slide portion 22 in the ink supply direction. The open/close valve contact portion 221 is formed in a cylindrical shape having an outer diameter smaller than an inner diameter of the open/close valve housing portion 112 of the first main body portion 11 at the downstream end thereof in the ink supply direction and an inner diameter larger than a diameter of the first open/close valve 12 at the downstream end thereof in the ink supply direction. An inner diameter of the open/close valve contact portion 221 at an upstream end thereof in the ink supply direction is equal to a diameter of the inclined portion 124 of the first open/close valve 12 at a substantially middle part thereof in the ink supply direction. Thus, in a case of connecting the ink container 382 to the container rack 381, the upstream end of the open/close valve contact portion 221 in the ink supply direction is inserted into the open/close valve housing portion 112 and pushes the first open/close valve 12 to the upstream side in the ink supply direction.

The seal member 222 is disposed at an outer circumferential part of the slide portion 22 between the first flange portion 223 on the upstream side in the ink supply direction and the second flange portion 224 on the downstream side in that direction. The seal member 222 is an O-ring formed of, for example, an elastic member of rubber or the like, and an inner circumferential part thereof is in tight contact with an outer circumferential surface of the slide portion 22. The seal member 222 has an outer diameter smaller than an inner diameter of the large inner diameter portion 211 of the second main body portion 21 and larger than an inner diameter of the small inner diameter portion 212 thereof.

The seal member 222 of the slide portion 22 is located in the large inner diameter portion 211 of the second main body portion 21 in the ink supply direction. When the slide portion 22 moves to the downstream side in the ink supply direction, an outer circumferential part of the seal member 222 comes in contact with an inner circumferential part of the small inner diameter portion 212 of the second main body portion 21. Thus, the air flow path Fa is closed at a location of the seal member 222. That is, the slide portion 22 opens/closes the air flow path Fa.

The air flow path Fa is disposed between the second main body portion 21 and the slide portion 22. Specifically, the air flow path Fa is constituted by a gap between an inner circumferential surface of the second main body portion 21 and the outer circumferential surface of the slide portion 22. As described earlier, when the slide portion 22 moves to the downstream side in the ink supply direction, the air flow path Fa is closed at the location of the seal member 222 and is disconnected from the ink flow path Fq. Furthermore, as will be described later, when the slide portion 22 moves to the upstream side in the ink supply direction in a state where the first main body portion 11 is inserted in the second main body portion 21, the air flow path Fa is connected to the ink flow path Fq. That is, the air flow path Fa is switched by movement of the slide portion 22 between a state of being connected to the ink flow path Fq and a state of being disconnected therefrom.

In the slide portion 22, the first flange portion 223 is provided on a downstream side of the open/close valve contact portion 221 in the ink supply direction and on an upstream side of the disposition location of the seal member 222 in the ink supply direction. When the first main body portion 11 is inserted in the second main body portion 21, the first main body portion 11 comes in contact with a side surface of the first flange portion 223 facing the upstream side in the ink supply direction.

In the slide portion 22, the second flange portion 224 is provided on a downstream side of the disposition location of the seal member 222 in the ink supply direction. One end of the second biasing member 23 is in contact with a side surface of the second flange portion 224 facing the downstream side in the ink supply direction.

The second biasing member 23 is disposed on a downstream side of the second flange portion 224 of the slide portion 22 in the ink supply direction. The second biasing member 23 is formed of, for example, a compression coil spring, a coil axis of which extends along the center axis of the second main body portion 21, and the slide portion 22 is inserted in a coil center thereof.

An upstream end of the second biasing member 23 in the ink supply direction is in contact with the side surface of the second flange portion 224 facing the downstream side in the ink supply direction. A downstream end of the second biasing member 23 in the ink supply direction is in contact with a side surface of the stepped portion 214 in the second main body portion 21 facing the upstream side in the ink supply direction. As described earlier, the seal member 222 comes in contact with the inner circumferential part of the small inner diameter portion 212 of the second main body portion 21, and thus the air flow path Fa is closed at the location of the seal member 222 and is disconnected from the ink flow path Fq. The second biasing member 23 biases the slide portion 22 in such a direction as to connect the air flow path Fa to the ink flow path Fq.

With regard to the connection mechanism 1 for an ink flow path according to the first embodiment, in a case of connecting the ink container 382 to the container rack 381, the first main body portion 11 is inserted in the second main body portion 21. Thus, a distal end of the first main body portion 11 is brought into contact with a distal end of the slide portion 22. Specifically, at an initial stage of inserting the first main body portion 11 in the second main body portion 21, the downstream end of the first open/close valve 12 in the ink supply direction comes in contact with the upstream end of the slide portion 22 in the ink supply direction.

Further, as shown in FIG. 7, the slide portion 22 causes the first open/close valve 12 to move against a biasing force of the first biasing member 13 to open the first open/close valve 12. Specifically, the substantially middle part of the inclined portion 124 of the first open/close valve 12 in the ink supply direction comes in contact with the upstream end of the open/close valve contact portion 221 of the slide portion 22 in the ink supply direction. The ink passage grooves 121 extend from the downstream end to the upstream end of the inclined portion 124 in the ink supply direction, and thus even when the open/close valve contact portion 221 comes in contact with the inclined portion 124, the ink flow path Fq can be brought into an opened state by the ink passage grooves 121. Moreover, the slide portion 22 causes the first open/close valve 12 to move to the upstream side in the ink supply direction, and thus the outer circumferential part of the seal member 122 is separated from the inner circumferential part of the small inner diameter portion 1122 of the open/close valve housing portion 112, so that the part of the ink flow path Fq included in the first main body portion 11 is opened.

After that, the downstream end of the first main body portion 11 in the ink supply direction comes in contact with the side surface of the first flange portion 223 of the slide portion 22 facing the upstream side in the ink supply direction. Moreover, the first main body portion 11 causes the slide portion 22 to move against a biasing force of the second biasing member 23 to disconnect the air flow path Fa from the ink flow path Fq. Specifically, the first main body portion 11 causes the slide portion 22 to move to the downstream side in the ink supply direction, so that the outer circumferential part of the seal member 222 comes in contact with the inner circumferential part of the small inner diameter portion 212 of the second main body portion 21 to close the air flow path Fa, thus disconnecting the air flow path Fa from the ink flow path Fq.

Then, as shown in FIG. 7, communication is established between the part of the ink flow path Fq included in the first main body portion 11 and the part of the ink flow path Fq included in the slide portion 22. When the suction pump 384 is operated, a suction force thereof causes the first backflow prevention valve 14 to move to the downstream side in the ink supply direction against a biasing force of the third biasing member 15, and thus ink in the ink container 382 is supplied to the apparatus main body 310. When the suction pump 384 is stopped from being operated, a biasing force of the third biasing member 15 causes the first backflow prevention valve 14 to move to the upstream side in the ink supply direction, and thus a backflow of the ink can be prevented.

In a case of disconnecting the ink container 382 from the container rack 381, the first main body portion 11 is caused to move in such a direction as to be separated from the slide portion 22. Then, as shown in FIG. 8, a contact pressure between the first main body portion 11 and the slide portion 22 is decreased, so that the second biasing member 23 biases the slide portion 22 to move, thus connecting the air flow path Fa to the ink flow path Fq. Specifically, when the first main body portion 11 is caused to move in such a direction as to be separated from the slide portion 22, the downstream end of the first main body portion 11 in the ink supply direction is separated from the side surface of the first flange portion 223 of the slide portion 22 facing the upstream side in the ink supply direction. Moreover, the second biasing member 23 causes the slide portion 22 to move to the upstream side in the ink supply direction, so that the outer circumferential part of the seal member 222 is separated from the inner circumferential part of the small inner diameter portion 212 of the second main body portion 21 to open the air flow path Fa as shown in FIG. 8, thus connecting the air flow path Fa to the ink flow path Fq.

The air flow path Fa is connected to the ink flow path Fq, and thus a negative pressure related to suction of ink by the suction pump 384 as an action from the apparatus main body 310 (the container rack 381) causes air to flow through the ink flow path Fq in a direction directed from the ink container 382 toward the apparatus main body 310. Thus, ink remaining in the connection section of the ink flow path Fq can be actively caused to move toward the apparatus main body 310. Accordingly, leakage of ink remaining in the connection section of the ink flow path Fq can be suppressed more effectively.

In a state shown in FIG. 8, the outer circumferential part of the seal member 116 of the first main body portion 11 is in contact with the inner circumferential part of the large inner diameter portion 211 of the second main body portion 21. Thus, it is possible to prevent leakage of ink and air from the inside to the outside of each of the first main body portion 11 and the second main body portion 21. Furthermore, the outer circumferential part of the seal member 122 of the first main body portion 11 is separated from the inner circumferential part of the small inner diameter portion 1122 of the open/close valve housing portion 112. Thus, in the first main body portion 11, air can be caused to flow also through a region on a downstream side of the first backflow prevention valve 14 in the ink supply direction. Accordingly, by use of such an air flow, even ink remaining in the first main body portion 11 can be actively caused to move through the ink flow path Fq toward the apparatus main body 310.

Moreover, the first main body portion 11 is separated from the slide portion 22, so that the first biasing member 13 biases the first open/close valve 12 to close the part of the ink flow path Fq included in the first main body portion 11. Specifically, when the first main body portion 11 is separated from the slide portion 22, the first biasing member 13 causes the first open/close valve 12 to move to the downstream side in the ink supply direction, and thus the outer circumferential part of the seal member 122 comes in contact with the inner circumferential part of the small inner diameter portion 1122 of the open/close valve housing portion 112 to close the ink flow path Fq. Then, the first main body portion 11 is taken out from inside the second main body portion 21.

As in the above-described configuration, the first connection portion 10 includes the first backflow prevention valve 14 provided on an upstream side of the first open/close valve 12 in the ink supply direction. According to this configuration, it is possible to prevent a backflow of ink in a part of the ink flow path Fq included in the ink container 382. Furthermore, when the air flow path Fa is opened, in the first main body portion 11, air can be caused to flow also through the region on the downstream side of the first backflow prevention valve 14 in the ink supply direction.

Furthermore, in the connection mechanism 1, the second connection portion 20 also includes a second backflow prevention valve (the suction pump 384) provided on a downstream side in the ink supply direction. According to this configuration, it is possible to prevent a backflow of ink in a part of the ink flow path Fq included in the apparatus main body 310. Furthermore, the suction pump 384 is used as the second backflow prevention valve, and thus there is no need to separately prepare another member as the second backflow prevention valve, so that a cost reduction of the connection mechanism 1 can be achieved.

Figure 9:
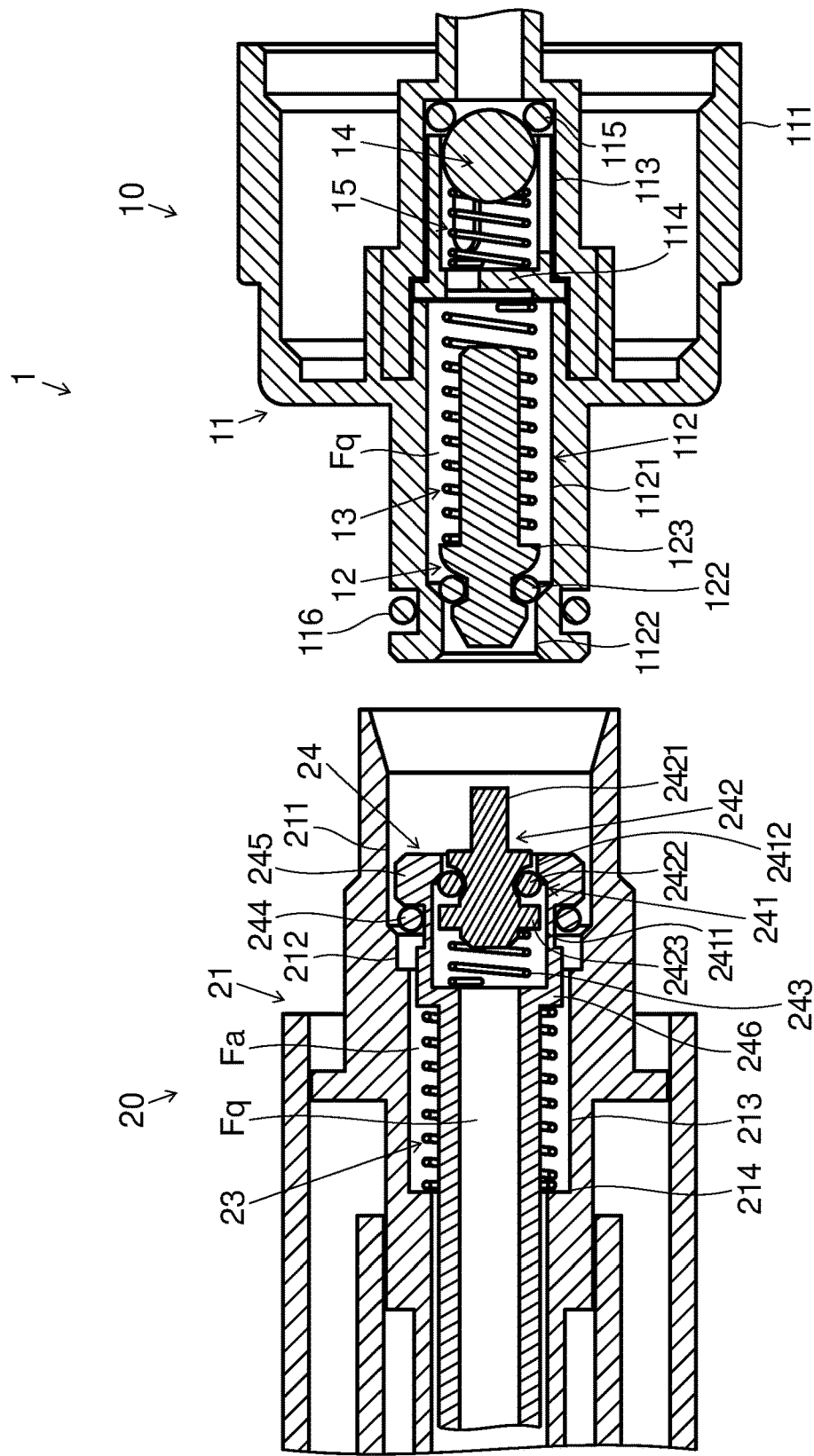
FIG. 9 is a sectional view showing a connection mechanism for an ink flow path according to a second embodiment of the present disclosure.
Figure 10:
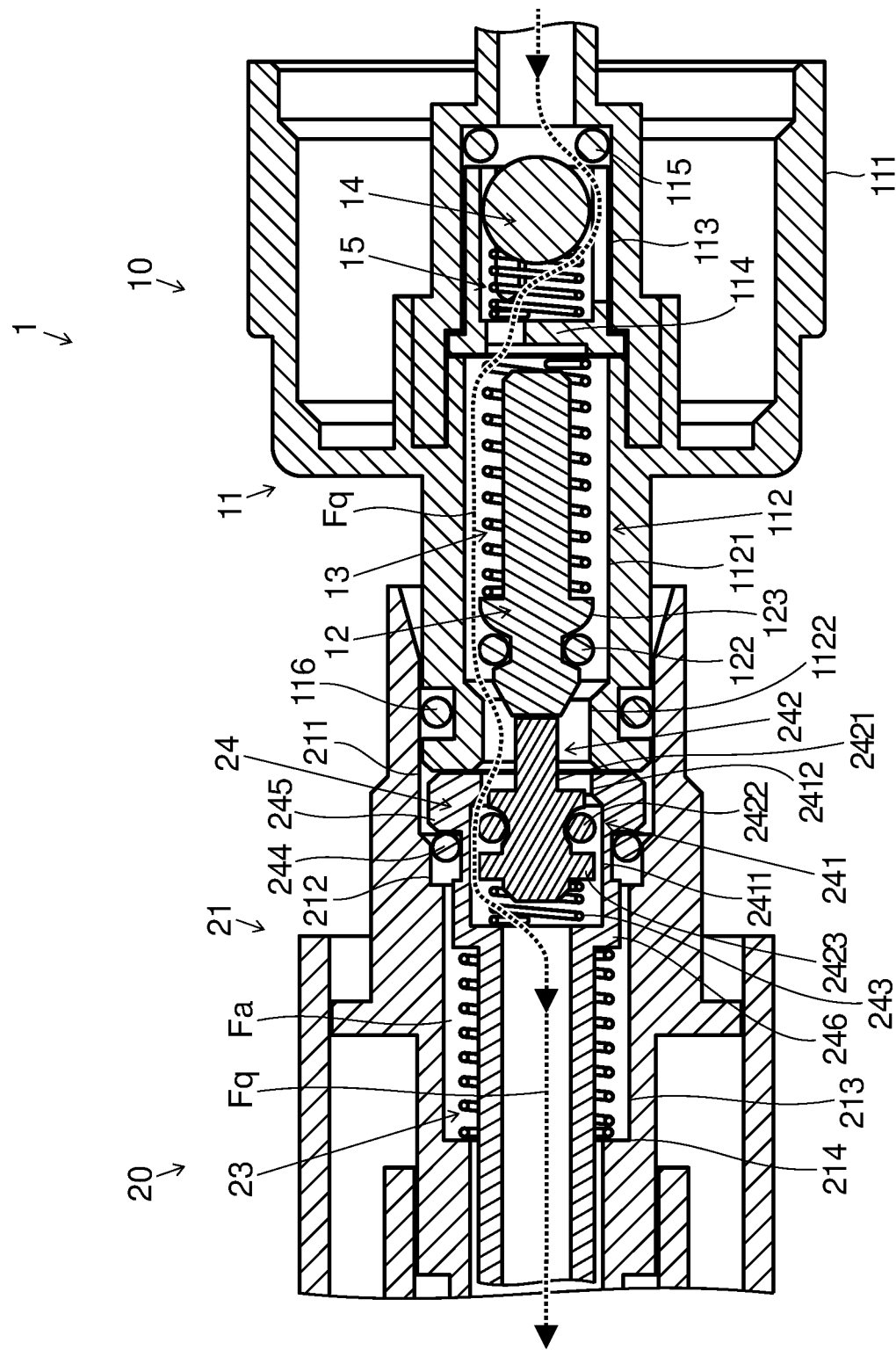
FIG. 10 is a sectional view showing the connection mechanism for an ink flow path according to the second embodiment of the present disclosure, which illustrates a state where communication of the ink flow path is established.
Figure 11:
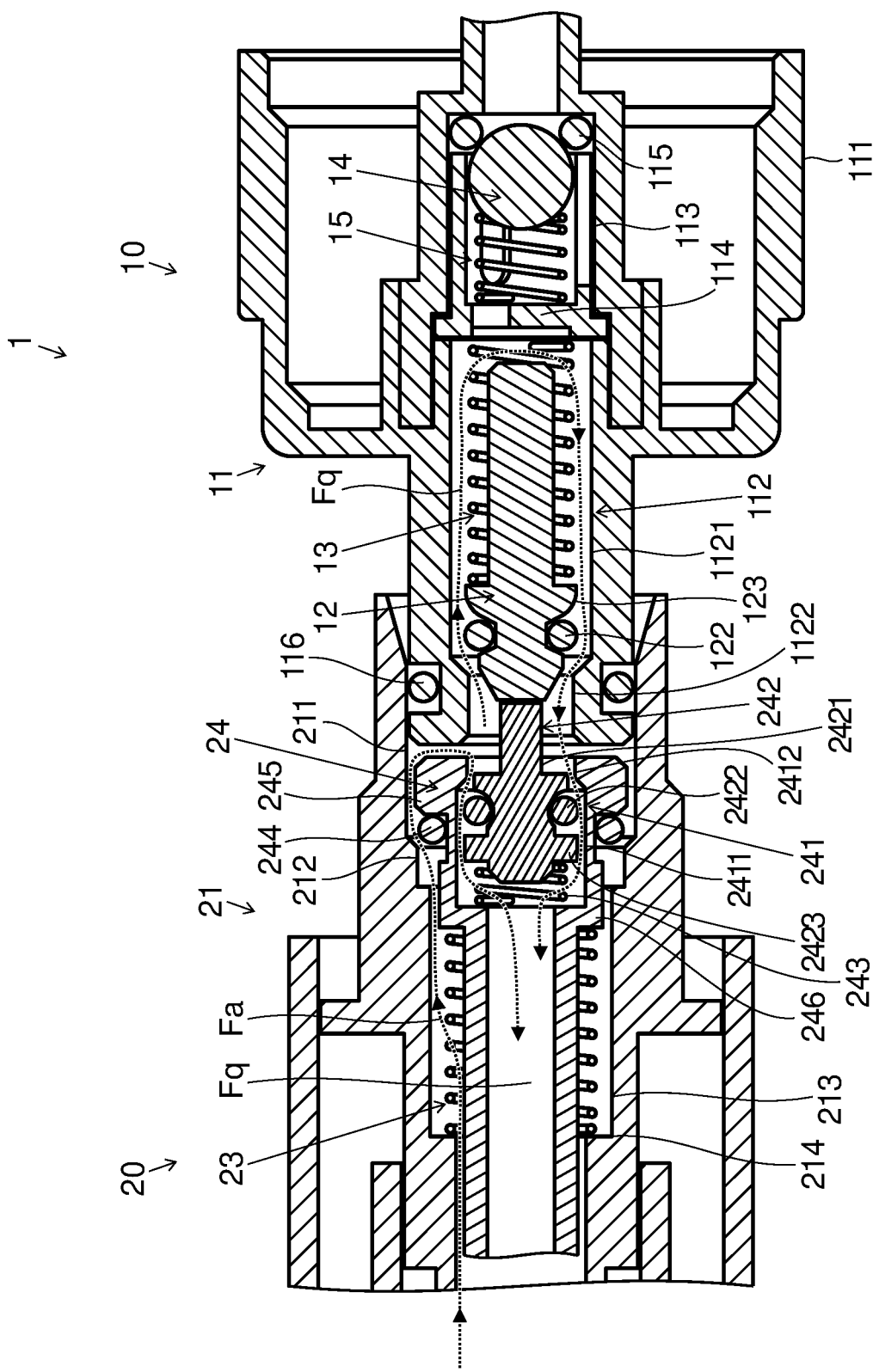
FIG. 11 is a sectional view showing the connection mechanism for an ink flow path according to the second embodiment of the present disclosure, which illustrates a state where an air flow path is connected to the ink flow path.

Next, with reference to FIG. 9, FIG. 10, and FIG. 11, a description is given of a configuration of a connection mechanism 1 for an ink flow path according to a second embodiment. FIG. 9 is a sectional view showing the connection mechanism 1 for an ink flow path Fq according to the second embodiment. FIG. 10 is a sectional view showing the connection mechanism 1 for the ink flow path Fq according to the second embodiment, which illustrates a state where communication of the ink flow path Fq is established. FIG. 11 is a sectional view showing the connection mechanism 1 for the ink flow path Fq according to the second embodiment, which illustrates a state where an air flow path Fa is connected to the ink flow path Fq. An ink supply direction is directed from a first connection portion 10 toward a second connection portion 20 in FIG. 9, FIG. 10, and FIG. 11. Since this embodiment is identical in basic configuration to the first embodiment described earlier, constituent elements in common may be denoted by identical reference characters or referred to identically, with duplicate descriptions thereof omitted, and configurations other than characterizing parts may not be described.

As shown in FIG. 9, FIG. 10, and FIG. 11, the connection mechanism 1 for an ink flow path (a liquid flow path) according to the second embodiment includes the first connection portion 10 and the second connection portion 20. The second connection portion 20 includes a second main body portion 21, a slide portion 24, and a second biasing member 23. The second connection portion 20 further includes the air flow path Fa.

The slide portion 24 includes an open/close valve housing portion 241, a second open/close valve 242, a fourth biasing member 243, a seal member 244, a first flange portion 245, and a second flange portion 246.

The open/close valve housing portion 241 is disposed at an upstream end of the slide portion 24 in the ink supply direction and at a radial center of the slide portion 24. The open/close valve housing portion 241 is formed in a cylindrical shape extending in the ink supply direction along a center axis of the slide portion 24. The second open/close valve 242 is housed in the open/close valve housing portion 241.

The open/close valve housing portion 241 includes therein a large inner diameter portion 2411 and a small inner diameter portion 2412. The large inner diameter portion 2411 has an inner diameter larger than that of the small inner diameter portion 2412. The small inner diameter portion 2412 is disposed on an upstream side of the large inner diameter portion 2411 in the ink supply direction so as to be continuous with the large inner diameter portion 2411. An upstream end of the small inner diameter portion 2412 in the ink supply direction is an upstream end of each of the slide portion 24 and the open/close valve housing portion 241 in the ink supply direction and is open to the outside. The large inner diameter portion 2411 has an inner diameter larger than an outer diameter of an after-mentioned seal member 2422 of the second open/close valve 242. The small inner diameter portion 2412 has an inner diameter smaller than an outer diameter of the seal member 2422 of the second open/close valve 242.

Most part of the second open/close valve 242 except for an open/close valve contact portion 2421 is housed in the open/close valve housing portion 241. That is, the second open/close valve 242 is disposed in the slide portion 24. The second open/close valve 242 is formed in substantially a rod shape extending along a center axis of the cylindrical open/close valve housing portion 241. In the open/close valve housing portion 241, the second open/close valve 242 is movable in the ink supply direction. The second open/close valve 242 includes the open/close valve contact portion 2421, the seal member 2422, and a flange portion 2423.

The open/close valve contact portion 2421 is provided at an upstream end of the second open/close valve 242 in the ink supply direction. The open/close valve contact portion 2421 is formed in a rod shape having an outer diameter smaller than an inner diameter of an open/close valve housing portion 112 of a first main body portion 11 at a downstream end thereof in the ink supply direction. Thus, in a case of connecting the ink container 382 to the container rack 381, the open/close valve contact portion 2421 is inserted into the open/close valve housing portion 112 and pushes a first open/close valve 12 to an upstream side in the ink supply direction.

The seal member 2422 is disposed at an outer circumferential part of the second open/close valve 242 on a downstream side of the open/close valve contact portion 2421 in the ink supply direction. The seal member 2422 is an O-ring formed of, for example, an elastic member of rubber or the like, and an inner circumferential part thereof is in tight contact with an outer circumferential surface of the second open/close valve 242. The seal member 2422 has an outer diameter smaller than an inner diameter of the large inner diameter portion 2411 of the open/close valve housing portion 241 and larger than an inner diameter of the small inner diameter portion 2412 thereof.

The seal member 2422 of the second open/close valve 242 is located in the large inner diameter portion 2411 of the open/close valve housing portion 241 in the ink supply direction. When the second open/close valve 242 moves to the upstream side in the ink supply direction, an outer circumferential part of the seal member 2422 comes in contact with an inner circumferential part of the small inner diameter portion 2412 of the open/close valve housing portion 241. Thus, an ink flow path Fq is closed at a location of the seal member 2422. That is, the second open/close valve 242 opens/closes the ink flow path Fq.

In the second open/close valve 242, the flange portion 2423 is provided on a downstream side of a disposition location of the seal member 2422 in the ink supply direction. One end of the fourth biasing member 243 is in contact with a side surface of the flange portion 2423 facing a downstream side in the ink supply direction.

The fourth biasing member 243 is disposed on a downstream side of the flange portion 2423 of the second open/close valve 242 in the ink supply direction. The fourth biasing member 243 is formed of, for example, a compression coil spring, a coil axis of which extends along a center axis of the open/close valve housing portion 241, and a downstream part of the second open/close valve 242 in the ink supply direction is inserted in a coil center thereof.

A downstream end of the fourth biasing member 243 in the ink supply direction is in contact with a side surface facing the upstream side at a downstream end in the open/close valve housing portion 241 in the ink supply direction. An upstream end of the fourth biasing member 243 in the ink supply direction is in contact with the side surface of the flange portion 2423 of the second open/close valve 242 facing the downstream side in the ink supply direction. As described earlier, the seal member 2422 comes in contact with the inner circumferential part of the small inner diameter portion 2412 of the open/close valve housing portion 241, and thus the ink flow path Fq is closed at the location of the seal member 2422. The fourth biasing member 243 biases the second open/close valve 242 in such a direction as to close the ink flow path Fq.

The seal member 244 is disposed at an outer circumferential part of the slide portion 24 between the first flange portion 245 on the upstream side in the ink supply direction and the second flange portion 246 on the downstream side in that direction. The seal member 244 is an O-ring formed of, for example, an elastic member of rubber or the like, and an inner circumferential part thereof is in tight contact with an outer circumferential surface of the slide portion 24. The seal member 244 has an outer diameter smaller than an inner diameter of a large inner diameter portion 211 of the second main body portion 21 and larger than an inner diameter of a small inner diameter portion 212 thereof. The slide portion 24 moves to open/close the air flow path Fa at a location of the seal member 244.

The first flange portion 245 is provided at the upstream end of the slide portion 24 in the ink supply direction and on an upstream side of the disposition location of the seal member 244 in the ink supply direction. When the first main body portion 11 is inserted in the second main body portion 21, the first main body portion 11 comes in contact with a side surface of the first flange portion 245 facing the upstream side in the ink supply direction.

In the slide portion 24, the second flange portion 246 is provided on a downstream side of the disposition location of the seal member 244 in the ink supply direction. One end of the second biasing member 23 is in contact with a side surface of the second flange portion 246 facing the downstream side in the ink supply direction.

With regard to the connection mechanism 1 for an ink flow path according to the second embodiment, in a case of connecting the ink container 382 to the container rack 381, the first main body portion 11 is inserted in the second main body portion 21. Thus, a distal end of the first main body portion 11 is brought into contact with a distal end of the slide portion 24. Specifically, at an initial stage of inserting the first main body portion 11 in the second main body portion 21, a downstream end of the first open/close valve 12 in the ink supply direction comes in contact with an upstream end of the open/close valve contact portion 2421 of the second open/close valve 242 in the ink supply direction.

Further, as shown in FIG. 10, the slide portion 24 causes the first open/close valve 12 to move against a biasing force of a first biasing member 13 to open the first open/close valve 12 so that a part of the ink flow path Fq included in the first main body portion 11 is opened. Specifically, the slide portion 24 causes the first open/close valve 12 to move to the upstream side in the ink supply direction, and thus an outer circumferential part of a seal member 122 is separated from an inner circumferential part of a small inner diameter portion 1122 of the open/close valve housing portion 112, so that the part of the ink flow path Fq included in the first main body portion 11 is opened.

Furthermore, the first open/close valve 12 causes the second open/close valve 242 to move against a biasing force of the fourth biasing member 243 to open the second open/close valve 242 so that a part of the ink flow path Fq included in the second main body portion 21 is opened. Specifically, the first open/close valve 12 causes the second open/close valve 242 to move to the downstream side in the ink supply direction, and thus the outer circumferential part of the seal member 2422 is separated from the inner circumferential part of the small inner diameter portion 2412 of the open/close valve housing portion 241, so that the part of the ink flow path Fq included in the second main body portion 21 is opened.

After that, a downstream end of the first main body portion 11 in the ink supply direction comes in contact with the side surface of the first flange portion 245 of the slide portion 24 facing the upstream side in the ink supply direction. Moreover, the first main body portion 11 causes the slide portion 24 to move against a biasing force of the second biasing member 23 to close the air flow path Fa, thus disconnecting the air flow path Fa from the ink flow path Fq.

Then, as shown in FIG. 10, communication is established between the part of the ink flow path Fq included in the first main body portion 11 and the part of the ink flow path Fq included in the slide portion 24.

In a case of disconnecting the ink container 382 from the container rack 381, the first main body portion 11 is caused to move in such a direction as to be separated from the slide portion 24. Then, as shown in FIG. 11, a contact pressure between the first main body portion 11 and the slide portion 24 is decreased, so that the second biasing member 23 biases the slide portion 24 to move, thus connecting the air flow path Fa to the ink flow path Fq.

Moreover, the first main body portion 11 is separated from the slide portion 24, so that the first biasing member 13 biases the first open/close valve 12 to close the part of the ink flow path Fq included in the first main body portion 11. Furthermore, when the first main body portion 11 is separated from the slide portion 24, the fourth biasing member 243 biases the second open/close valve 242 to close the part of the ink flow path Fq included in the second main body portion 21. Then, the first main body portion 11 is taken out from inside the second main body portion 21.

In the foregoing second embodiment, the second connection portion 20 includes the second open/close valve 242 that is disposed in the slide portion 24 and opens/closes the ink flow path Fq. According to this configuration, in a case of disconnecting the ink container 382 from the container rack 381, a part of the ink flow path Fq included in the apparatus main body 310 (a part thereof included in the container rack 381) can be closed. This makes it possible to use air flowing through the air flow path Fa to actively cause ink remaining in a connection section of the ink flow path Fq to move toward the apparatus main body 310 and also to effectively suppress leakage of ink remaining in the connection section of the ink flow path Fq.

Furthermore, according to the foregoing embodiments, the inkjet recording apparatus 300 includes the connection mechanism 1 for the ink flow path Fq, which is configured as above and disposed in the connection section of the ink flow path Fq between the apparatus main body 310 and the ink container 382, and thus in the inkjet recording apparatus 300, ink remaining in said connection section can be actively caused to move toward the apparatus main body 310. Accordingly, in the inkjet recording apparatus 300, leakage of ink remaining in the connection section of the ink flow path Fq can be suppressed more effectively.

While the foregoing has described the embodiments of the present disclosure, the scope of the present disclosure is not limited thereto, and the present disclosure can be implemented by adding various modifications thereto without departing from the spirit of the disclosure.

What is claimed is:

1. A connection mechanism for a liquid flow path disposed in a connection section of the liquid flow path between an apparatus main body and a container that contains a liquid to be supplied to the apparatus main body through suction of the liquid as an action from the apparatus main body and is mountable/demountable with respect to the apparatus main body, the connection mechanism comprising:
   a first connection portion that is provided in the container; and
   a second connection portion that is provided in the apparatus main body, the first connection portion being mountable/demountable to/from the second connection portion,
   wherein
   the first connection portion includes:
      a first main body portion that includes therein a part of the liquid flow path;
      a first open/close valve that is disposed in the first main body portion and opens/closes the liquid flow path; and
      a first biasing member that biases the first open/close valve in such a direction as to close the liquid flow path,
   the second connection portion includes:
      a second main body portion;
      a slide portion that is disposed in the second main body portion so as to be movable relative to the second main body portion and includes therein another part of the liquid flow path;
      an air flow path that is disposed between the second main body portion and the slide portion and is switched by movement of the slide portion between a state of being connected to the liquid flow path and a state of being disconnected from the liquid flow path; and
      a second biasing member that biases the slide portion in such a direction as to connect the air flow path to the liquid flow path,
   in a case of connecting the container to the apparatus main body, the first main body portion is inserted in the second main body portion so that a distal end of the first main body portion is brought into contact with a distal end of the slide portion, the slide portion causes the first open/close valve to move against a biasing force of the first biasing member to open the first open/close valve, thus establishing communication between the part of the liquid flow path included in the first main body portion and the other part of the liquid flow path included in the slide portion, and the first main body portion causes the slide portion to move against a biasing force of the second biasing member to disconnect the air flow path from the liquid flow path, and
   in a case of disconnecting the container from the apparatus main body, a contact pressure between the first main body portion and the slide portion is decreased, so that the second biasing member biases the slide portion to move, thus connecting the air flow path to the liquid flow path, the first main body portion is separated from the slide portion, so that the first biasing member biases the first open/close valve to close the part of the liquid flow path included in the first main body portion, and then the first main body portion is taken out from inside the second main body portion.

2. The connection mechanism for a liquid flow path according to claim 1, wherein
   the first connection portion includes a first backflow prevention valve that is provided on an upstream side of the first open/close valve in a liquid supply direction.

3. The connection mechanism for a liquid flow path according to claim 1, wherein
   the second connection portion includes a second open/close valve that is disposed in the slide portion and opens/closes the liquid flow path.

4. The connection mechanism for a liquid flow path according to claim 1, further comprising:
   a second backflow prevention valve that is provided on a downstream side of the second connection portion in a liquid supply direction.

5. The connection mechanism for a liquid flow path according to claim 4, wherein
   a suction pump is used as the second backflow prevention valve.

6. An inkjet recording apparatus, comprising:
   the apparatus main body that performs image formation with ink;
   the container that contains an ink liquid to be supplied to the apparatus main body and is mountable/demountable with respect to the apparatus main body; and
   the connection mechanism for a liquid flow path according to claim 1, which is disposed in a connection section of an ink flow path between the apparatus main body and the container.

7. An inkjet recording apparatus, comprising:
   the apparatus main body that performs image formation with ink;
   the container that contains an ink liquid to be supplied to the apparatus main body and is mountable/demountable with respect to the apparatus main body; and
   the connection mechanism for a liquid flow path according to claim 2, which is disposed in a connection section of an ink flow path between the apparatus main body and the container.

8. An inkjet recording apparatus, comprising:
   the apparatus main body that performs image formation with ink;
   the container that contains an ink liquid to be supplied to the apparatus main body and is mountable/demountable with respect to the apparatus main body; and
   the connection mechanism for a liquid flow path according to claim 3, which is disposed in a connection section of an ink flow path between the apparatus main body and the container.

9. An inkjet recording apparatus, comprising:
   the apparatus main body that performs image formation with ink;
   the container that contains an ink liquid to be supplied to the apparatus main body and is mountable/demountable with respect to the apparatus main body; and
   the connection mechanism for a liquid flow path according to claim 4, which is disposed in a connection section of an ink flow path between the apparatus main body and the container.

10. An inkjet recording apparatus, comprising:
    the apparatus main body that performs image formation with ink;
    the container that contains an ink liquid to be supplied to the apparatus main body and is mountable/demountable with respect to the apparatus main body; and the connection mechanism for a liquid flow path according to claim 5, which is disposed in a connection section of an ink flow path between the apparatus main body and the container.

\* \* \* \* \*